(12) United States Patent
Callaghan

(10) Patent No.: US 9,445,772 B2
(45) Date of Patent: Sep. 20, 2016

(54) REDUCED RADIATION FLUOROSCOPIC SYSTEM

(75) Inventor: Frank Callaghan, Blaine, MN (US)

(73) Assignee: St. Jude Medical, Atrial Fibrillatin Division, Inc., St. Paul, MN (US)

( * ) Notice: Subject to any disclaimer, the term of this patent is extended or adjusted under 35 U.S.C. 154(b) by 1996 days.

(21) Appl. No.: 11/967,400

(22) Filed: Dec. 31, 2007

(65) Prior Publication Data

US 2009/0171321 A1  Jul. 2, 2009

(51) Int. Cl.
*A61B 5/05* (2006.01)
*A61B 6/12* (2006.01)
*A61B 6/00* (2006.01)

(52) U.S. Cl.
CPC . *A61B 6/12* (2013.01); *A61B 5/05* (2013.01); *A61B 6/466* (2013.01); *A61B 6/488* (2013.01); *A61B 6/542* (2013.01)

(58) Field of Classification Search
CPC ........ A61B 6/12; A61B 6/4441; A61B 5/05; A61B 6/00; A61B 6/542; A61B 2017/00247
USPC ....... 600/411, 424, 425, 427, 435, 421–423; 382/128, 285, 294; 250/370.09; 378/4
See application file for complete search history.

(56) References Cited

U.S. PATENT DOCUMENTS

| | | | |
|---|---|---|---|
| 5,297,549 A | 3/1994 | Beatty et al. | |
| 5,369,678 A | 11/1994 | Chiu et al. | |
| 5,409,000 A | 4/1995 | Imran | |
| 5,638,501 A | 6/1997 | Gough et al. | |
| 5,697,377 A | 12/1997 | Wittkampf | |
| 6,048,362 A | 4/2000 | Berg | |
| 6,115,626 A | 9/2000 | Whayne et al. | |
| 6,493,575 B1 | 12/2002 | Kesten et al. | |
| 6,556,695 B1 | 4/2003 | Packer et al. | |
| 6,650,729 B2 * | 11/2003 | Braess et al. | 378/108 |
| 6,650,927 B1 | 11/2003 | Keidar | |
| 6,712,836 B1 | 3/2004 | Berg et al. | |
| 6,856,827 B2 | 2/2005 | Seeley et al. | |
| 7,234,225 B2 | 6/2007 | Johnson et al. | |
| 7,235,070 B2 | 6/2007 | Vanney | |
| 7,250,049 B2 | 7/2007 | Roop et al. | |
| 7,263,397 B2 | 8/2007 | Hauck et al. | |
| 2005/0027193 A1 * | 2/2005 | Mitschke et al. | 600/427 |

OTHER PUBLICATIONS

Rehani et al. Radiation effects in fluoroscopically guided cardiac interventions—keeping them under control. International Journal of Cardiology. 109:147-151. Jul. 19, 2005.*
International Search Report and Written Opinion for PCT/US2008/087129 mailed Feb. 3, 2009.

* cited by examiner

*Primary Examiner* — Joel Lamprecht
(74) *Attorney, Agent, or Firm* — Dykema Gossett PLLC

(57) ABSTRACT

An imaging system includes a display, an x-ray based image acquisition device, a workstation, and a medical device, e.g., a catheter. The image acquisition device is configured to obtain real-time two-dimensional images of a portion of a patient's body that is disposed within the field of view of the image acquisition device. The workstation is configured to integrate and register a three-dimensional model of an anatomic structure with the two-dimensional image, and to provide the display with a real-time image of the integrated image. The catheter includes a distal portion that comprises a radiopaque material. The image acquisition device is further adapted to apply radiation at a first dosage rate that is below a second dosage rate sufficient to detect anatomic structures.

23 Claims, 3 Drawing Sheets

REDUCED RADIATION FLUOROSCOPIC SYSTEM

BACKGROUND OF THE INVENTION a. Field of the Invention

The present invention relates to x-ray based imaging systems. More particularly, the present invention relates to a reduced radiation fluoroscopic imaging system in which a three-dimensional model of an internal anatomic structure of a patient is integrated and registered with a two-dimensional fluoroscopic image generated by a fluoroscope.

b. Background Art

It is known that a wide variety of imaging systems can be used to assist a clinician/physician in the performance of various catheter-based diagnostic and therapeutic procedures relating to different parts of the human anatomy, such as, for example, the heart. One conventional imaging method is fluoroscopy. In fluoroscopy, a fluoroscope is used to provide clinicians/physicians with real-time two-dimensional images of internal anatomic structures of a patient. The fluoroscope further provides a means for monitoring the location and position of medical instruments, such as catheters, that are disposed within the patient at locations within the field of view of the fluoroscope during the performance of a particular procedure.

In general terms, a fluoroscope consists of a radiation source (i.e., x-ray source) and a fluorescent screen. In practice, a patient is placed between the radiation source and the screen, and x-rays are directed toward the particular region of the patient's body that is within the field of view of the fluoroscope and that a clinician/physician wishes to image. As the x-rays pass through or are absorbed by the patient, images are created on the fluorescent screen. The fluoroscope may also include a monitor electrically connected to the screen upon which the images may be displayed. One drawback of fluoroscopy, however, is that it provides relatively poor anatomic detail due, at least in part, to the two-dimensional images that it creates. Additionally, to provide useful images, the patient and/or the clinician/physician performing the procedure or operating the fluoroscope may be exposed to relatively high doses of radiation, which is considered to be undesirable for both the patient and/or the clinician/physician.

Other conventional imaging methods include computed tomography (CT) and magnetic resonance (MR) imaging. In these methods, a patient is scanned in a CT or MR imaging instrument in order to acquire image data relating to particular internal anatomic structures of the patient. Using various techniques and software, the acquired image data can be processed and a three-dimensional model of desired anatomic structures can be generated. While these methods are useful in obtaining high quality and detailed images of particular internal structures of a patient, they also are not without their drawbacks. For instance, by themselves, these methods cannot assist a physician in catheter-based procedures being performed on a patient since they do not allow sufficient visualization for the navigation and guidance of certain types of catheters. More particularly, these systems do not readily provide real-time images that can be used to monitor the location and movement of the catheter relative to the internal structures of the patient's body.

As a result of the aforementioned drawbacks of conventional imaging systems, technology has been developed that combines the advantages of each of the above described imaging methodologies. Such technology includes integrating and registering the three-dimensional model created by the CT or MR methods, with the continuous real-time generation of two-dimensional images by the fluoroscope. By combining the respective methodologies, a clinician/physician is able to view detailed three-dimensional anatomic models superimposed on the real-time two-dimensional image in order to enhance the anatomic detail, while at the same time, monitoring the location and movement of the catheters or other instruments using the two-dimensional real-time fluoroscope image as he/she moves catheters within the patient. Accordingly, this technology adds improved anatomic visualization to conventional two-dimensional imaging systems, and catheter visualization and guidance to the three-dimensional modeling systems.

However, as with the methodologies described above, the current state of this particular technology has its disadvantages. For instance, as described above with respect to conventional fluoroscopic techniques, since fluoroscopy is required to visualize catheter location and movement, the patient and/or the clinician/physician are exposed undesirable amounts of radiation to adequately or sufficiently image the catheters in the patient. Another disadvantage or deficiency is that the current technology does not allow for mapping of the modeled anatomic structure. In other words, physiological and/or electrophysiological data relating to the modeled anatomic structure that is acquired by the catheter cannot be superimposed or otherwise displayed or visualized on the three-dimensional image.

Accordingly, there is a need for an imaging system that will minimize and/or eliminate one or more of the above-identified deficiencies.

BRIEF SUMMARY OF THE INVENTION

In various aspects, the present invention is directed to one or more components of an imaging system. The imaging system includes a display, an x-ray based image acquisition device, a workstation, and a medical device (e.g., a catheter). The image acquisition device is configured to obtain real-time two-dimensional images of a portion of a patient's body that is disposed within the field of view of the image acquisition device. The workstation is configured to integrate and register a three-dimensional model of an anatomic structure with the two-dimensional image, and to provide the display with a real-time image of the integrated image. The catheter includes a distal portion that comprises a radiopaque material. The image acquisition device is further adapted to apply radiation at a first dosage rate that is below a second dosage rate sufficient to detect anatomic structures. In an exemplary embodiment, the imaging system further includes a controller that is configured to control the amount of radiation emitted from the image acquisition device.

The present invention is further directed to a method of imaging a catheter in an anatomic structure. A first step of the method includes providing a model of the anatomic structure. A second step includes creating a fluoroscopic image of the anatomic structure in real-time. This is accomplished by applying radiation at a first radiation dosage rate, wherein the dosage rate is sufficient to provide an image of the anatomic structure. A third step includes integrating the model with the fluoroscopic image to provide an integrated image. In a fourth step, the integrated image is displayed on a display. Finally, a second radiation is applied at a second radiation dosage rate, wherein the second dosage rate is below the first dosage rate.

The foregoing and other aspects, features, details, utilities, and advantages of the present invention will be apparent

DETAILED DESCRIPTION OF THE INVENTION

Figure 1:
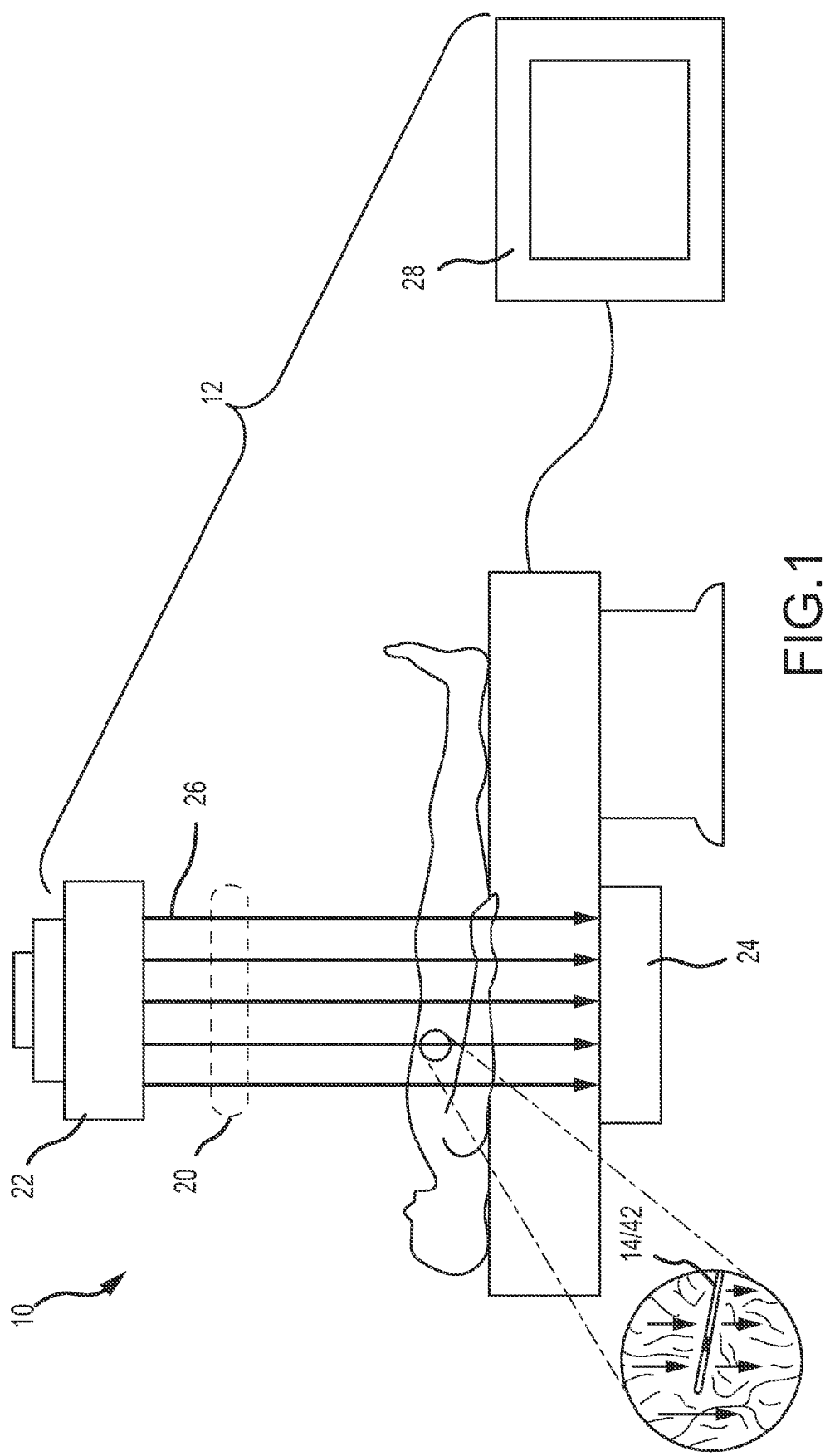
FIG. 1 is a diagrammatic view of an imaging system in accordance with the present invention.

Referring now to the drawings wherein like reference numerals are used to identify identical components in the various views, FIG. 1 illustrates an imaging system 10 in accordance with the present invention. Imaging system 10 is configured and operative to image desired internal anatomic structures of a patient. In the most general sense, imaging system 10 includes an image acquisition device 12 and one or more catheters 14. More particularly, as will be described in greater detail below, image acquisition device 12 is a x-ray based device, such as a fluoroscope, and at least a portion of catheter 14 is opaque to the x-rays emitted by image acquisition device 12.

In an exemplary embodiment, image acquisition device 12 is configured to acquire a detailed and highly accurate three-dimensional model of one or more particular internal anatomic structures from an imaging instrument, which, as will be described below, may be part of image acquisition device 12 or may be separate and distinct therefrom. Image acquisition device 12 is further configured to integrate this three-dimensional model of a desired structure with a two-dimensional real-time image of the desired structure and the region of the patient's body within which the modeled structure is located. For ease of description purposes alone, the following description will be directed to the imaging/modeling of the heart. It should be noted, however, that the present invention is not limited to such an application. Rather, one of ordinary skill in the art will recognize and appreciate that the present invention may find application in the imaging/modeling of other internal anatomic structures and/or in the performance of any number of diagnostic or therapeutic procedures.

The aforementioned integration enables a clinician/physician to view a detailed representation of the heart (i.e., the three-dimensional model superimposed on the real-time two-dimensional image), while contemporaneously monitoring the location and movement of catheter 14 disposed within the patient (i.e., the real-time two-dimensional image). Clinicians/physicians may then use the integrated images to perform various diagnostic and therapeutic procedures on the heart (e.g., cardiac mapping, cardiac ablation, electrophysiological (EP) studies, etc.).

Figure 2:
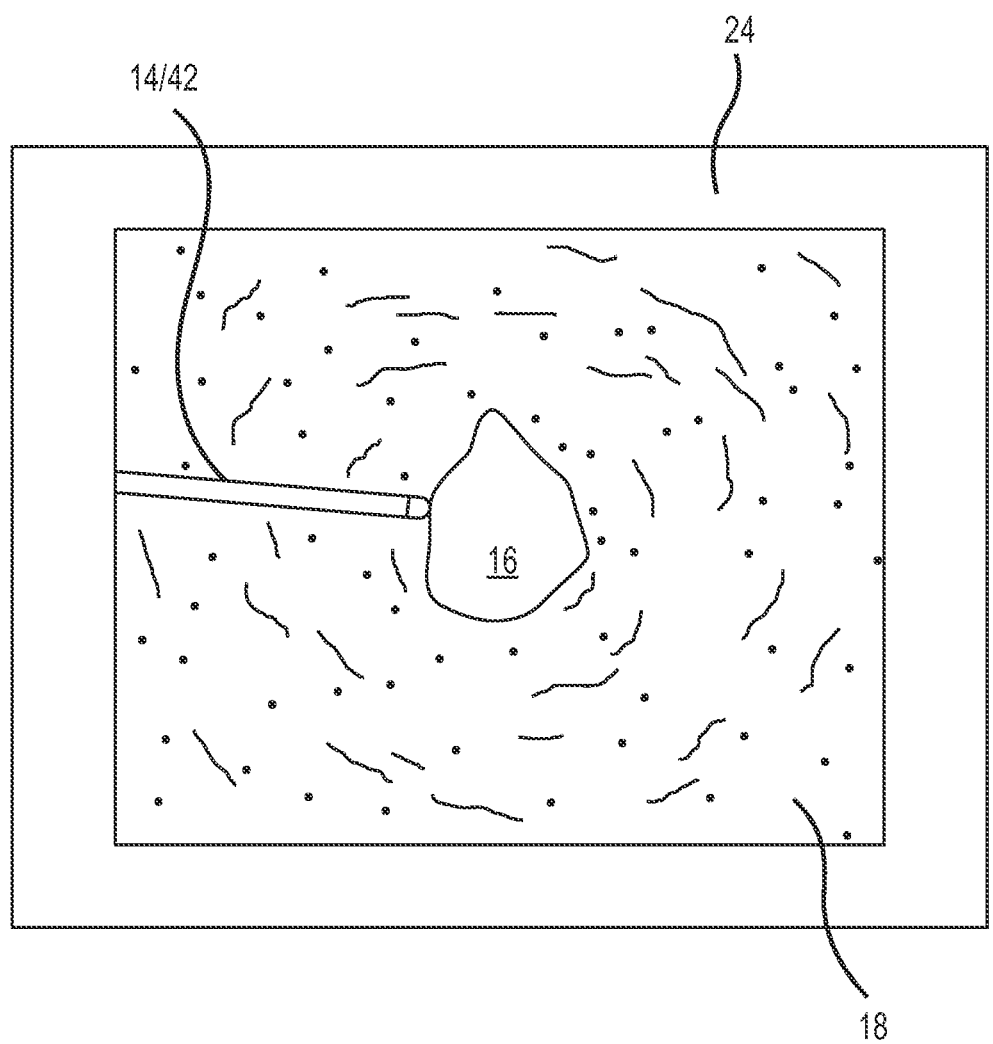
FIG. 2 is an enlarged view of the monitor component of the imaging system illustrated in FIG. 1.

The integration process includes a number of steps. A first step comprises acquiring a three-dimensional model 16 of the heart or a particular portion thereof (FIG. 2 shows a representation of model 16). Model 16 may be acquired using a number of techniques now known or hereafter developed. For instance, in one embodiment, the patient is scanned using a computed tomography (CT) or magnetic resonance (MR) imaging instrument, which is typically a separate and distinct device from image acquisition device 12. Using these instruments, image data relating to the desired anatomic structure is acquired in the form of scan slices. The scan slices are then segmented, using known techniques and software, to generate a computer-based model 16.

Data defining model 16 can then be saved (e.g., written to a CD, DVD, etc., or saved to a location accessible from image acquisition device 12) or transmitted directly to image acquisition device 12. It should be understood that as used herein, "model" will refer to the data defining the model of the structure, or a graphical representation thereof.

In an alternate embodiment, model 16 is generated using angiography or rotational angiography techniques. In such an embodiment, a radiopaque dye is injected into the patient's bloodstream. An arm of image acquisition device 12 having a radiation source associated therewith is then rotated about the patient to acquire image data corresponding to the desired structure of the heart. The image data is then used by image acquisition device 12 to generate model 16. Therefore, in this embodiment, a separate imaging instrument is not required to generate model 16, rather image acquisition device 12 itself generates model 16. Model 16 can also be generated using other anatomical mapping techniques known in the art, including magnetic based mapping or electroanatomical based mapping.

Accordingly, it will be appreciated by those skilled in the art that multiple techniques/methodologies exist that can be used to generate and/or acquire a three-dimensional model of the heart.

A second step in the integration process includes acquiring a real-time two-dimensional image of a particular portion of a patient's anatomy disposed with a field of view 20 of image acquisition device 12. Therefore, as illustrated in FIG. 1, the patient is placed onto image acquisition device 12 having a field of view 20. If image acquisition device 12 is used to generate model 16, the patient may be positioned onto image acquisition device 12 prior to the generation of model 16. If, however, model 16 is generated by a separate imaging instrument, then the patient is positioned on image acquisition device 12 subsequent to the commencement of the model generation process. A particular portion of the patient's body that is dependent on the positioning of the patient relative to field of view 20 is imaged. In addition to being dependent on the field of view, and the position of the patient relative thereto, what anatomic structures are ultimately imaged is also dependent on the sensitivity of image acquisition device 12. Accordingly, image acquisition device 12 must be appropriately calibrated such that it is sufficiently sensitive to distinguish differences in density of various soft tissues, bone, etc., so that the desired structures may be accurately imaged.

Image acquisition device 12 further includes a radiation source 22 and a screen or sensor 24 that is spaced apart from radiation source 22 by a distance sufficient to allow a typical size range of human patients to be positioned therebetween. Radiation source 22 is configured to direct x-rays 26 toward sensor 24 at certain dosage rates, and defines field of view 20. For purposes of explanation and illustration only, field of view 20 is illustrated in FIG. 1 as being defined by the emissive range of radiation source 22, however, the present invention is not limited to such a configuration. As x-rays 26 are directed toward sensor 24 at a dosage rate sufficient to image anatomic structures, the x-rays 26 either pass through or are alternatively absorbed in varying degrees by anatomic structures in the patient's body, a real-time two-dimensional image 18 revealing the constituent structure of the imaged region of the patient's body is created on screen/sensor 24. The x-rays 26 may also reveal the presence and location of medical instruments disposed within the imaged region, such as one or more catheters 14. Image acquisition device 12 may further include a controller that may be used to control the amount of radiation that is emitted by radiation source 22 by, for example, the clinician/physician adjusting the settings of the controller. As will be described below, once an adequate image of the anatomic structures is generated, the dosage rate of the radiation may be reduced.

In an exemplary embodiment, image acquisition device 12 still further includes a monitor 28 that is electrically connected to sensor 24. Accordingly, once two-dimensional image 18 is created, it may be communicated to monitor 28 for display. It should be noted that while in the above-described embodiment monitor 28 is part of image acquisition device 12, the present invention is not so limited. Rather, in alternate embodiments, monitor 28 may be electrically connected to image acquisition device 12, but may be a separate and distinct component of imaging system 10.

A third step in the integration process, which is performed subsequent to acquiring model 16 and acquiring two-dimensional image 18, includes importing and integrating model 16 into two-dimensional image 18. The process may include accessing model 16 from a storage location, such as a CD, DVD, storage drive, etc., that is either internal or external to image acquisition device 12. Once model 16 is imported, it may be viewed on monitor 28 within two-dimensional image 18 (See FIG. 2) and moved around (i.e., translated) and rotated within image 18 as desired. Model 16 may also be scaled (e.g., made larger or smaller) in accordance with the clinician/physician's preferences. This manipulation of model 16 allows for the clinician/physician to obtain the most accurate alignment between model 16 and the position and location of the heart in two-dimensional image 18 (i.e., the model of the heart is aligned with the silhouette of the heart depicted in two-dimensional image 18). While the foregoing steps of aligning model 16 to image 18 are largely manual, it is recognized that automated methods of alignment which employ numerical methods are well known in the art and can also be employed. A detailed description of at least one such method can be found in U.S. Pat. No. 6,556,695 entitled Method for Producing High Resolution Real-Time Images, of Structure and Function During Medical Procedures, issued to Packer et al. and assigned to Mayo Foundation for Medical Education and Research, which is hereby incorporated by reference in its entirety. In an exemplary embodiment, one or more catheters 14 may be used to assist in the scaling, translating and rotation of the model.

Once model 16 has been imported and accurately aligned as described above, a fourth step of registering model 16 with two-dimensional image 18 is performed. Model 16 may be registered with image 18 by the clinician/physician taking an affirmative action such as, for example, pressing or depressing a button, clicking a computer mouse, or issuing a command from a keyboard. Once model 16 is registered with real-time two-dimensional image 18, as the viewing angle of image acquisition device 12 is adjusted, model 16 rotates in synchrony with two-dimensional image 18, and vice versa.

Once model 16 and image have been registered, a fifth step may be employed in which the registration of model 16 with image 18 is verified. In one embodiment, this step entails increasing the radiation dosage rate to acquire an image of the anatomic structure that is adequately clear or detailed to allow for the verification that model 16 is, in fact, still appropriately aligned with the corresponding structure in image 18. Once the alignment is verified, the radiation dosage rate may be once again reduced. This step may be periodically performed during the performance of a procedure.

While the integration of model 16 with two-dimensional image 18 provides the advantages described above relating to improved anatomic and catheter visualization and guidance, the use of conventional x-ray based imaging systems and techniques, and fluoroscopic techniques in particular, exposes the patient and/or the clinician/physician to certain levels of radiation that are required to generate model 16. The x-ray exposure used is chosen (e.g., in magnitude and duration) so as to provide an image of anatomic structures (e.g., the heart and the surrounding tissue) and the medical instruments (e.g., catheters) that are disposed within field of view 20 of image acquisition device 12. It would be desirable to reduce the intensity of radiation to which the patient and clinician/physician are exposed, while at the same time maintaining the ability to monitor the location and movement of the catheter(s). It would also be desirable to be able to visualize, display or otherwise represent various electrophysiological and/or physiological data acquired by catheter 14 on model 16 in the form of, for example, color coding various portions of model 16. This would provide the clinician/physician as much information about the modeled structure as possible, or at least as much information as is needed.

In order to reduce the radiation to which the patient and/or clinician/physician are exposed, catheter 14 is constructed such that at least a portion thereof is sufficiently opaque to x-rays to increase the contrast between the catheter and the surrounding anatomic structures, even at reduced radiation levels. Because model 16 provides a highly accurate representation of the heart and is not dependent on the two-dimensional imaging of image acquisition device 12, there is less of a need to acquire high quality two-dimensional images of the heart or the surrounding area. Therefore, the primary purpose of the real-time two-dimensional image 18 during much of the procedure is to monitor the location and movement of catheter 14, not to image the heart. By making catheter 14 substantially radiopaque, the x-ray intensity required to image/visualize catheter 14 may be substantially reduced. For example, catheter 14 is sufficiently radiopaque such that it can be detected/imaged and distinguished from anatomic structures at radiation dosage rates that are insufficient to detect/image anatomic structures, such as, for example, soft tissue. Accordingly, while a first radiation dosage rate may be required to image the anatomic structure to allow for the integration of model 16, the dosage rate may be reduced once the model is integrated to a dosage rate that allows for the visualization of the radiopapque catheter. Therefore, because less radiation is required to image/visualize catheter 14, the amount of radiation to which the patient and the clinician/physician are exposed is reduced.

Figure 3:
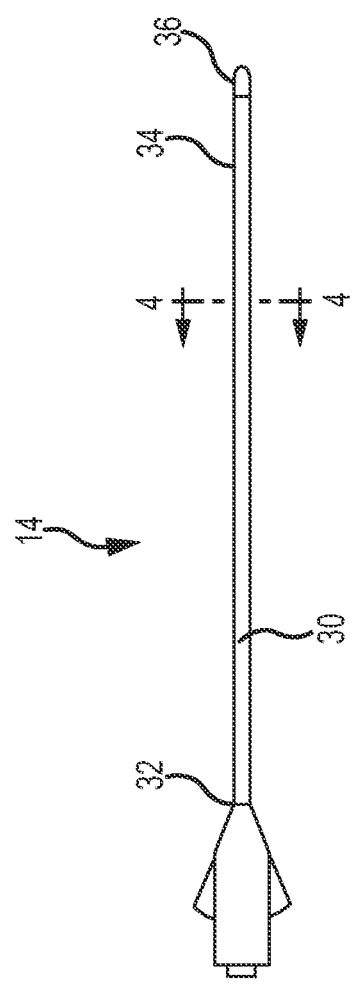
FIG. 3 is a diagrammatic view of a catheter of the imaging system illustrated in FIG. 1.
Figure 4:
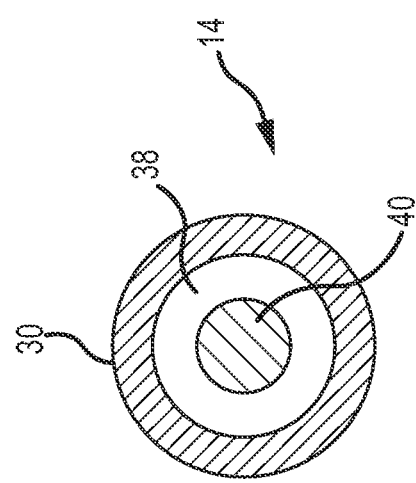
FIG. 4 is a cross-section view of the catheter illustrated in FIG. 3 taken substantially along the line 4-4 in FIG. 3.

Accordingly, with reference to FIG. 3, catheter 14 includes a distal portion which may include a shaft portion 30 having a proximal end 32 and a distal end 34. In an exemplary embodiment, catheter 14 further includes one or more elements 36 for performing diagnostic and/or therapeutic procedures (e.g., an electrode, a needle, an ultrasound transducer, etc.) mounted to, formed in, or otherwise associated with shaft 14 at or near distal end 34, for example. With reference to FIG. 4, which is a cross-section view of shaft 30, catheter 14 may still further include at least one lumen 38 disposed within shaft 30 within which one or more components 40 may be housed. For instance, electrical wires corresponding to element(s) 36, planarity wires, pull wires, and other components commonly disposed within a lumen of a catheter may be disposed within lumen 38.

In an exemplary embodiment, shaft 30 is comprised of a material that renders catheter 14 substantially radiopaque. More specifically, at least a portion of shaft 30 is formed of a combination of a polymeric material and a radiopaque compound. Examples of suitable compounds include barium sulfate, bismuth trioxide, bismuth subcarbonate, bismuth oxychloride, and zirconium dioxide. It should be noted, however, that this list is provided for exemplary purposes only and is not an exhaustive list of suitable materials. Rather, those of ordinary skill in the art will recognize that other compounds may exist that would be adequate to render catheter 14, and shaft 30 and/or any constituent components 40 thereof in particular, sufficiently radiopaque so as to allow for the detection/imaging of catheter 14 at radiation dosage rates that are so low that anatomic structures cannot be detected/imaged.

In an alternate embodiment at least a portion of one or more of components 40 is formed of a radiopaque material, such as a radiopaque metal. More specifically, one or more wires disposed within lumen 38 may be made of a metallic material that has sufficient radiopacity to render catheter 14 sufficiently radiopaque. Examples of suitable materials include tantalum, tungsten, gold, platinum, iridium, and platinum-iridium. It should be noted, however, that this list is provided for exemplary purposes only and is not an exhaustive list of suitable materials. Rather, those of ordinary skill in the art will recognize that other metals may exist that would be adequate to render component(s) 40, and therefore, catheter 14, sufficiently radiopaque so as to allow for the detection/imaging of catheter 14 at radiation dosage rates that are so low that anatomic structures cannot be detected/imaged.

In still a further embodiment, a combination of at least a portion of shaft 30 and a portion of component(s) 40 are both radiopaque in accordance with the description set forth above, such that catheter 14 is rendered sufficiently radiopaque so as to allow for the detection/imaging of catheter 14 at radiation dosage rates that are so low that anatomic structures cannot be detected/imaged.

In yet still a further embodiment, rather than a portion of catheter 14 and/or a portion of one or more components 40 being radiopaque, a radiopaque material can be transmitted in lumen 38, thereby rendering catheter 14 radiopaque.

Figure 5:
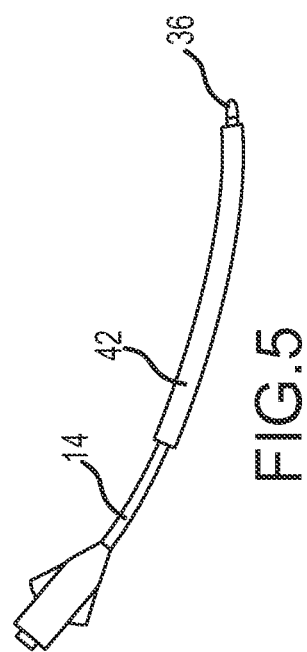
FIG. 5 is a diagrammatic view of a sheath employed in an exemplary embodiment of the imaging system illustrated in FIG. 1.

In an alternate embodiment of imaging system 10, and as depicted in FIG. 5, rather than catheter 14 being sufficiently radiopaque, a sheath 42 having a body 44 and a passageway 46 into which catheter 14 is inserted and within which catheter 14 travels to a desired location within the patient's body, is substantially radiopaque. As with shaft 30, in an exemplary embodiment, at least a portion of sheath 42 is formed of a combination of a polymeric material and a radiopaque compound. Examples of suitable compounds include barium sulfate, bismuth trioxide, bismuth subcarbonate, bismuth oxychloride, and zirconium dioxide. It should be noted, however, that this list is provided for exemplary purposes only and is not an exhaustive list of suitable materials. Rather, those of ordinary skill in the art will recognize that other compounds may exist that would be adequate to render sheath 42 sufficiently radiopaque so as to allow for the detection/imaging of sheath 42 at radiation dosage rates that are so low that anatomic structures cannot be detected/imaged. It should be noted that while a sheath for use with a catheter is described above with particularity, it will be appreciated by those of ordinary skill in the art that a sheath such as sheath 42 may be used in conjunction with any number of medical instruments other than a catheter. Accordingly, the present invention is not meant to be limited to sheath for use with a catheter, but rather such an arrangement is provided for exemplary purposes only.

In alternate embodiments, combinations of sheath 42, shaft 30, and/or components 40 are radiopaque so as to render catheter 14 sufficiently radiopaque to be visualized at lower levels of radiation than that normally necessary to visualize anatomic structure.

Whether shaft 30, components 40 and/or sheath 42 are radiopaque, the degree of such radiopacity, and the level of the radiation intensity required, is dependent on the application in connection with catheter 14 is to be used. Therefore, one of ordinary skill in the art will appreciate and recognize that this invention generally finds application in any number of procedures/applications such as, for example, cardiac mapping, cardiac ablation, electrophysiological studies, etc. Accordingly, in order to determine which of shaft 30, components 40 and/or sheath 42 are radiopaque, the degree of radiopacity, and the required the intensity of the radiation, one of ordinary skill in the art would employ the following methodology to assess the various criteria that must be considered for the particular procedure/application.

A first consideration involves the contrast of two-dimensional image 18. More particularly, one must establish what degree of contrast is needed for the particular procedure being performed. In other words, to what level of detail must catheter 14 be visualized to optimally perform the desired procedure (i.e., is it sufficient to see the contour of the catheter alone, or is it necessary to distinguish where the various sensors or electrodes are on the catheter, etc.).

A second, and somewhat related consideration involves determining whether it is also necessary or desirable to visualize elements 36 associated with catheter 14, and/or whether it is necessary or desirable to distinguish elements 36 from shaft 30, for example. Whether elements 36 are to be visualized and/or distinguished will dictate, for example, the type of material to be used.

A third consideration involves the sensitivity of the equipment. One must determine the sensitivity of the imaging equipment. A machine that is highly sensitive will require less radiation to visualize the catheter, and consequently, a less radiopaque catheter may be suitable, and vice versa.

A fourth consideration involves the level of radiation exposure that can be tolerated. One must determine the ideal maximum desired radiation intensity/dosage rate to which a patient and/or clinician/physician can/should be exposed. The more radiation that can be tolerated, the less radiopaque the catheter may be, and vice versa.

A fifth consideration is whether the imaging necessarily has to be "real-time" or whether a certain amount of lag time between the acquisition of the image data and the presentation of the corresponding image on the screen may be permissible. If "real-time" is not necessarily required, a lower level of radiation intensity may be used to produce a lower contrast image. That image may then be enhanced using software or other postprocessing techniques to provide an image that is suitable for the intended purpose. Accordingly, because at least measure of lag time is permitted in such an instance, the catheter could be less radiopaque and the radiation intensity/dosage rate may be reduced to generate an image that may be enhanced in a subsequent process. If, on the other hand, "real-time" is needed, higher levels of radiation intensity and/or radiopaqueness would be required to provide an image that necessitates little or no enhancement/postprocessing such that the image can be provided immediately.

When each of these criteria/considerations are taken into account, the structure to be made radiopaque and the material from which that structure is formed may be selected in order to create a catheter that is optimal for the specific application in connection with which the catheter is to be used. It should be noted that while the criteria set forth above were identified with specificity, those of ordinary skill in the art will appreciate that criteria other than those set forth above may also be taken into consideration, and therefore, remain within the spirit and scope of the present invention.

Accordingly, as set forth above, the use of a sufficiently radiopaque catheter or sheath provides the advantage of reduced radiation exposure to the patient and/or clinician/physician alike. Additionally, because a three-dimensional model is registered with the two-dimensional image and a radiopaque catheter may be tracked/monitored using the two-dimensional image, an added advantage is that catheter navigation is tracked in three-dimensions. Accordingly, there is no longer a need for typical navigation and visualization systems that include additional sensors placed in strategic locations on the patient's body that assist in the monitoring and navigation of the catheter.

As briefly mentioned above, it may be desirable to be able to visualize, display or otherwise represent various electrophysiological and/or physiological data acquired by catheter 14 on model 16. Accordingly, one such image acquisition device 12 is utilized with known visualization, navigation and mapping systems, such as, for example, the EnSite NavX® system that is commercially available from St. Jude Medical, Inc., and as is seen by reference to U.S. Pat. No. 7,263,397 entitled "Method and Apparatus for Catheter Navigation and Location and Mapping in the Heart" to Hauck et al., owned by the common assignee of the present invention, and hereby incorporated by reference in its entirety. More specifically, as catheter 14 visits various locations of the heart, electrodes or sensors that comprise elements 36 are configured to acquire/measure physiological and/or electrophysiological data (e.g., electrograms of the heart) corresponding thereto. For instance, elements 36 may acquire various indicators or metrics of an electrogram (e.g., amplitude, timing, frequency or any other of a number of attributes). The acquired data is directly or indirectly communicated, in one form or another, from catheter 14 to image acquisition device 12. Image acquisition device 12 is configured to process this data and then, using software and other techniques that are known to those of ordinary skill in the art, cause the acquired data to be represented/visualized on model 16, and displayed on display 28.

Alternatively, rather than the data being communicated from catheter 14 to image acquisition device 12, the data may be sent to a separate controller and/or workstation that is distinct from image acquisition device 12 and that is configured to, among other things, process electroanatomic data. In such an instance, the controller or workstation processes the data and then displays it on display 28 or another display associated with the workstation. More particularly, once the data is processed by the workstation, a map may be generated corresponding to the acquired data. The map may then be integrated with the images and/or models described above at image acquisition device 12 or at the workstation, and then displayed.

Accordingly, in an exemplary embodiment, image 18 created by image acquisition device 12 may be transformed into a digitized map and communicated to the workstation where it may be displayed. Model 16 may also be communicated to the workstation where it may be integrated and registered with image 18. The electroanatomic data acquired by catheter 14 may then be represented on model 16. Alternatively, the electroanatomic data may be used to generate model 16, which is then integrated and registered with image 18 at the workstation.

Additionally, the controller, which may be considered a breakout box, may also be used to control the amount of radiation that is emitted by image acquisition device 12, either on its own, at the direction of the clinician/physician, or at the control of the workstation, for example. Accordingly, in this instance, image acquisition device 12 would be electrically connected to the breakout box. It will be appreciated by those of ordinary skill in the art that while the description above is directed to an arrangement wherein the workstation and controller are separate and distinct components from image acquisition device 12, in an alternate embodiment, one or both of these components is integral to image acquisition device 12. Accordingly, the present invention is not meant to be limited to solely to the arrangement described above.

In one exemplary embodiment, the various data acquired at the particular areas of the heart visited by catheter 14 and that correspond to model 16 are represented on model 16 by color coding the respective areas of model 16 in accordance with a predetermined color coding scheme. In an alternate embodiment, other known forms of coding and data presentation techniques may be used in place of color coding to allow for the visualization of the acquired data. Accordingly, the present invention adds a mapping aspect to imaging system 10 that previously was not available.

Although only certain embodiments of this invention have been described above with a certain degree of particularity, those skilled in the art could make numerous alterations to the disclosed embodiments without departing from the spirit or scope of this invention. For example, model 16 may be generated using other methods than described above. Further, radiopaque catheter 14 may be constructed of any number and/or types of materials that would render catheter 14 radiopaque, and/or find application in a system other than a fluoroscopic based system. Still further, various types of mapping/data coding may be employed to represent the acquired data on model 16. Additionally, all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An imaging system comprising
a display;
an x-ray based image acquisition device having a field of view and configured to obtain a real-time two-dimensional image of a region of a patient's body disposed within said field of view, wherein said region includes an anatomic structure of said patient;
a workstation adapted to integrate and register a three-dimensional model of said anatomic structure-with said two-dimensional image and to provide the display with a real-time image of the integrated image; and
a medical device with a distal portion, said distal portion comprising a radiopaque material;
wherein said image acquisition device is adapted to apply radiation at a first radiation dosage rate to detect said anatomic structure and said distal portion of said medical device, and to reduce said radiation to a second radiation dosage rate to continue to detect said distal portion of said medical device, wherein said image acquisition device is configured to reduce said radiation to said second radiation dosage rate based on a level of radiation intensity that does not exceed a minimum radiation intensity required to detect said distal portion of said medical device comprising said radiopaque material, wherein said second radiation dosage rate is below a level sufficient to detect said anatomic structure.

2. The imaging system in accordance with claim 1 wherein said image acquisition device is adapted such that said second dosage rate is a predetermined dosage rate.

3. The imaging system in accordance with claim 1 further comprising a controller adapted to allow for at least said second dosage rate to be set during a procedure performed on said patient.

4. The imaging system in accordance with claim 1 wherein said anatomic structure is the patient's heart.

5. The imaging system in accordance with claim 1 wherein said medical device comprises a catheter, and said distal portion of said catheter includes
a shaft; and
a lumen disposed within said shaft in which a component is disposed;
wherein at least one of a portion of said shaft and a portion of said component comprises said radiopaque material.

6. The imaging system in accordance with claim 5 wherein said distal portion of said catheter includes an element associated with said shaft, said element adapted to acquire data relating to said anatomic structure represented by said three-dimensional model.

7. The imaging system in accordance with claim 6 wherein said display is adapted to display said two-dimensional image, said three-dimensional model, and said distal portion of said catheter, and wherein said workstation is further adapted to process said data and to represent said data on said three-dimensional model on said display.

8. The imaging system of claim 7 wherein said workstation is adapted to color code said three-dimensional model to represent said data in accordance with a predetermined color-coding scheme.

9. The imaging system of claim 1 wherein said medical device comprises a catheter, and further wherein said catheter includes a shaft and an element associated with said shaft, said element adapted for use in an ablation procedure.

10. The imaging system of claim 1 further comprising an instrument adapted to generate said three-dimensional model of said anatomic structure, said workstation further adapted such that data corresponding to said model can be imported into said workstation.

11. The imaging system of claim 10 wherein said instrument comprises one of a CT and MR imaging instrument.

12. The imaging system of claim 1 wherein said instrument comprises an electroanatomical mapping system.

13. The imaging system of claim 1 wherein said workstation is configured to generate said three-dimensional model.

14. The imaging system of claim 1 wherein said image acquisition device is a fluoroscope.

15. The imaging system in accordance with claim 1 wherein said medical device comprises one of a catheter and a sheath.

16. An imaging system comprising
a display;
a controller configured to control the amount of radiation emitted from an x-ray image acquisition device;
a workstation adapted to integrate and register a three-dimensional model of an anatomic structure of a patient with a two-dimensional image created by said image acquisition device that includes an image of said anatomic structure, and to provide said display with a real-time image of the integrated image; and
a medical device with a distal portion, said distal portion comprising a radiopaque material,
wherein said controller is adapted to apply radiation at a first radiation dosage rate to detect said anatomic structure and said distal portion of said medical device, and to reduce said radiation to a second radiation dosage rate to continue to detect said distal portion of said medical device, wherein said controller is configured to reduce said radiation to said second radiation dosage rate based on a level of radiation intensity that does not exceed a minimum radiation intensity required to detect said distal portion of said medical device comprising said radiopaque material, wherein said second radiation dosage rate is below a level sufficient to detect said anatomic structure.

17. The imaging system in accordance with claim 16 wherein said medical device comprises a catheter, and said distal portion of said catheter includes an element adapted to acquire data relating to said anatomic structure represented by said three-dimensional model.

18. The imaging system in accordance with claim 17 wherein said display is adapted to display said two-dimensional image, said three-dimensional model, and said distal portion of said catheter, and wherein said workstation is further adapted to process said data and to represent said data on said three-dimensional model on said display.

19. The imaging system of claim 16 further comprising an instrument adapted to generate said three-dimensional model of said anatomic structure, said workstation further adapted such that data corresponding to said model can be imported into said workstation.

20. The imaging system in accordance with claim 16 wherein said medical device comprises one of a catheter and a sheath.

21. A method of imaging a medical device in an anatomic structure comprising
providing a model of the anatomic structure;
creating a fluoroscopic image of the anatomic structure in real-time by applying radiation at a first radiation dosage rate, wherein the first radiation dosage rate is sufficient to provide an image of the anatomic structure and a distal portion of the medical device comprising a radiopaque material;
integrating said model with said fluoroscopic image to provide an integrated image;
displaying said integrated image on a display; and
reducing said radiation to apply radiation at a second radiation dosage rate to continue to image said distal portion of the medical device, wherein said reduction in said radiation to said second radiation dosage rate is based on a level of radiation intensity that does not exceed a minimum radiation intensity required to image said distal portion of the medical device comprising said radiopaque material, wherein said second radiation dosage rate is sufficient to image said radiopaque material in said distal portion of the medical device and insufficient to image the anatomic structure.

22. The method in accordance with claim 21 wherein said providing step includes the substep of generating a three-dimensional model of said structure.

23. The method in accordance with claim 21 further comprising tracking the position of the medical device on said display at said second radiation dosage rate.

* * * * *